United States Patent [19]

Cohen et al.

[11] 4,033,845
[45] July 5, 1977

[54] [2-(4-OXO-4H-1-BENZOPYRAN-2-YL)E-THENYL]BENZONITRILES AND BENZOIC ACIDS

[75] Inventors: Marvin P. Cohen, New Milford; John Shavel, Jr., Mendham; Max von Strandtmann, Rockaway Township, Morris County, all of N.J.

[73] Assignee: Warner-Lambert Company, Morris Plains, N.J.

[22] Filed: Nov. 20, 1975

[21] Appl. No.: 633,761

[52] U.S. Cl. .................. 260/240 D; 260/345.2; 260/345.5; 424/283
[51] Int. Cl.² ............................. C07D 311/22
[58] Field of Search .......... 260/240 D, 345.2, 345.5

[56] References Cited
UNITED STATES PATENTS

| 3,598,840 | 8/1971 | Majoie | 260/345.2 |
| 3,786,071 | 1/1974 | Cairns et al. | 260/345.2 |
| 3,825,574 | 7/1974 | Brown | 260/345.2 |
| 3,872,108 | 3/1975 | Ukyo et al. | 260/345.2 |
| 3,896,114 | 7/1975 | Nohara et al. | 260/345.2 |

FOREIGN PATENTS OR APPLICATIONS

| 1,493,967 | 2/1969 | Germany |
| 1,042,192 | 9/1966 | United Kingdom |
| 1,049,289 | 11/1966 | United Kingdom |

OTHER PUBLICATIONS

Koo, J. Org. Chem. 26 (1961) pp. 2440-2442.

*Primary Examiner*—Arthur P. Demers
*Attorney, Agent, or Firm*—Albert H. Graddis; Frank S. Chow

[57] ABSTRACT

The present invention relates to [2-(4-oxo-4H-1-benzopyran-2-yl)ethenyl]benzonitrile and benzoic acids having the following structural formula:

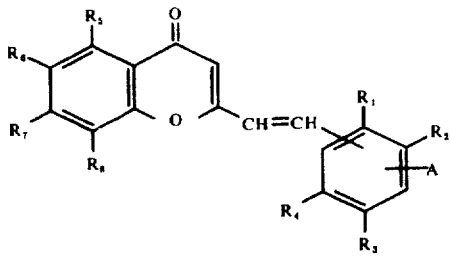

in which $R_1$, $R_2$, $R_3$, $R_4$, $R_5$, $R_6$, $R_7$ and $R_8$ are hydrogen, lower alkyl, halogen or lower alkoxy, and A is COOH or CN. The compounds of this invention exhibit anti-allergy properties and are indicated in the management of allergic manifestations such as bronchial asthma.

11 Claims, No Drawings

[2-(4-OXO-4H-1-BENZOPYRAN-2-YL)ETHENYL]-BENZONITRILES AND BENZOIC ACIDS

The present invention relates to [2-(4-oxo-4H-1-benzopyran-2-yl)ethenyl]benzonitriles and benzoic acids having the following structural formula:

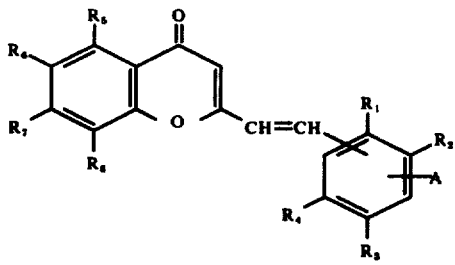

wherein $R_1$ to $R_8$ are hydrogen, lower alkyl, halogen or lower alkoxy, and A is COOh or CN.

In the above definitions for $R_1$ to $R_8$, lower alkyl and the lower alkyl portions of lower alkoxy are meant to embrace straight-or branched-chain alkyl radicals of 1–6 carbon atoms, for example, methyl, ethyl, propyl, isopropyl, n-butyl, n-amyl, n-hexyl, ethylbutyl, 2,3-dimethylbutyl, and so on. Halogen means chlorine, bromine, iodine and fluorine.

The above compounds exhibit anti-allergy properties in mammals. Thus, in tests conducted according to procedures described in I. Mota, *Life Sciences*, 7: 465 (1963) and Z. Ovary, O. Bier, Proc. Soc. Exptl. Biol. Med., 81: 584 (1952), they were found to prevent allergic and asthmatic reactions in rats at dosage levels of about 25 mg/kg intraperitoneally. These compounds are, therefore, indicated in the management of bronchial asthma, hay fever and other similar allergic conditions.

The compounds of the present invention can be administered orally and by such compositions as tablets, pills, dispersible powders, capsules, and the like. The active ingredient is mixed with at least one inert pharmaceutical diluent such as lactose, forming granules, using agents such as water or alcohol, and the resulting granules compressed into tablets utilizing standard tabletting procedures.

Liquid pharmaceutically administerable compositions are prepared by dissolving or suspending the active ingredient in a pharmaceutically acceptable carrier such as water or syrup. In addition, the compounds of this invention can be administered by inhalation thereby in which the compound is formulated by standard aerosol technique.

To treat allergic manifestations, the compounds of this invention are typically administered in dosages varying between 10–25 mg per kg of body weight two to three times daily. The precise dosage regimen can be varied depending on the mode of administration, the condition being treated and the host to whom the administration is being made, by methods well-known to the healing arts.

According to the present invention the above compound I is prepared by treating a compound of the formula:

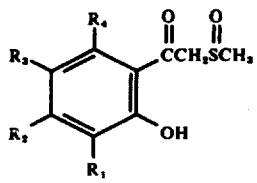

-continued
with a compound of the formula:

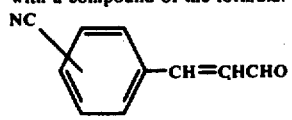

in which $R_1$ – $R_4$ have the same meaning as defined above.

Acidic hydrolysis of compounds of Structure I in which A is CN yields those compounds of this invention in which A is carboxy.

As will be obvious to those skilled in the art, the compounds of this invention in which A is carboxy can be readily converted to other derivatives, for example, to the corresponding esters by reacting with an alcohol, e.g., methanol, ethanol, etc., or to salts, by reacting with a base, e.g., sodium, potassium or calcium hydroxide.

Starting compounds of Formula II are prepared in accordance with the description set out in Patent 3,801,664 and starting compounds of Formula III are prepared by the disclosure in H. Fecht, Chem. Ber. 40, 3898 (1907).

To further illustrate the practice of this invention, the following examples are included:

EXAMPLE 1

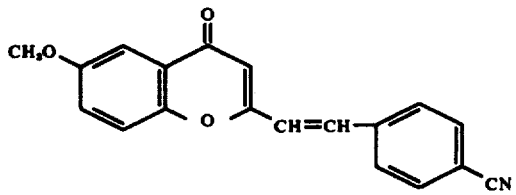

4-[2-(6-methoxy-4H-1-benzopyran-2-yl)ethenyl]benzonitrile

This was prepared by reacting 11.4g of 2'-hydroxy-5'-methoxy-2-(methylsulfinyl)acetophenone with 7.85g of p-cyanocinnamaldehyde in analogous fashion to 4-[2-(8-methoxy-4-oxo-4H-1-benzopyran-2-yl)ethenyl]benzonitrile. The material was recrystallized from toluene. mp 224°–26°; yield 6.5g (43%); λ max mμ (ε) 224 (20,600), 294 (21,900), 332 (43,500); ν max 820 (m), 980 (ms), 1080 (m), 1290 (m), 1580 (m), 1620 (s), 1645 (s), 2240 (m) cm$^{-1}$.

Anal. Calcd. for $C_{19}H_{13}NO_3$: C, 75.24; H, 4.32; N, 4.62. Found: C, 75.17; H, 4.44; N, 4.56.

EXAMPLE 2

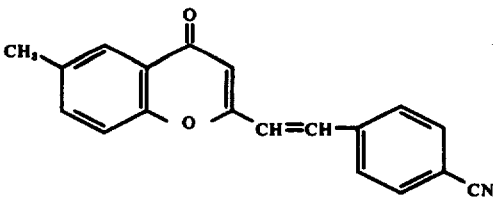

4-[2-(6-Methyl-4-oxo-4H-1-benzopyran-2-yl)ethenyl]-benzonitrile

This was prepared by reacting 6.36g of 2'-hydroxy-5'-methyl-2-(methylsulfinyl)acetophenone with 6.36g of p-cyanocinnamaldehyda in analogous fashion to 4-[2-(8-methoxy-4-oxo-4H-1-benzopyran-2-yl)ethenyl]benzonitrile. The material was recrystallized from toluene, mp 249°–51°; yield 3.5g (41%) λ max mμ (ε) 219 (19,300); 278 (13,500), 339 (41,000); ν max 825 (m), 980 (m), 1235 (m), 1580 (m), 1630 (m), 1670 (s), 2240 (m) cm$^{-1}$.

Anal. Calcd. for $C_{19}H_{13}NO_2$: C, 79.43; H, 4.56; N, 4.88. Found: C, 79.27; H, 4.59; N, 4.94.

EXAMPLE 3

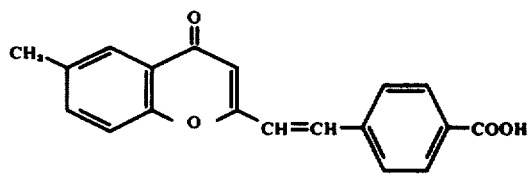

4-[2-(6-Methyl-4-oxo-4H-1-benzopyran-2-yl)ethenyl] benzonitrile and 50ml of 50% $H_2SO_4$ was refluxed for 1 hr. The mixture was chilled, and the solid filtered, washed with cold $H_2O$, and recrystallized from glacial acetic acid, mp 308°–12°; yield 1.5g (70%); λ max mμ (ε) 271 (10,800), 334 (37,300); ν max 770 (ms), 825 (m), 980 (m), 1170 (m), 1225 (s), 1580 (m), 1610 (s), 1710 (ms) cm$^{-1}$.

Anal. Calcd. for $C_{19}H_{14}O_4$: C, 74.45; H, 4.60. Found: C, 74.04; H, 4.66.

EXAMPLE 4

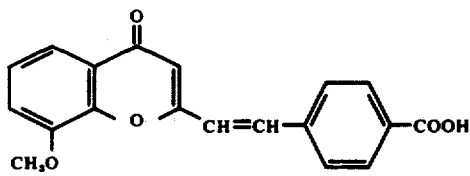

4-[2-(3-Methoxy-4-oxo-4H-1-benzopyran-2-yl)ethenyl]-benzoic acid

A mixture of 4g of 4-[(8-methoxy-4-oxo-4H-1-benzopyran-2-yl)ethenyl] benzonitrile and 100ml of 50% sulfuric acid was refluxed for 1 hr. The mixture was chilled, and the solid filered, washed with cold $H_2O$ and recrystallized from DMF, mp 298°–300°; yield 3g (70%); λ max mμ (ε) 211 (18,700), 333 (41,000); ν max 740 (m), 800 (m), 1060 (m), 1185 (m), 1650 (s), 1700 (ms) cm$^{-1}$.

Anal. Calcd. for $C_{19}H_{14}O_3$: C, 70.80; H, 4.38. Found: C, 70.73; H, 4.50.

EXAMPLE 5

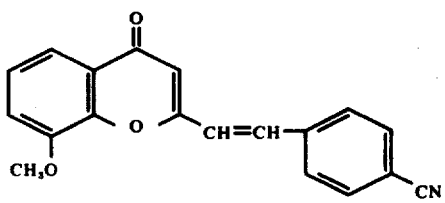

4-[2-(8-Methoxy-4-oxo-4H-1-benzopyran-2-yl)ethenyl]benzonitrile

A mixture of 7.85g of 4-cyanocinnamaldehyde (U.S. Pat. No. 2,993,834), 11.4g of 2'-hydroxy-3'-methoxy-2-(methylsulfinyl)acetophenone, 250ml of toluene, and 0.5ml of piperidine was refluxed for 3 hrs. The mixture was chilled, and the crystalline ppt. filtered, and recrystallized from toluene, mp. 274°–75°; yield 7g (46%); λ max mμ (ε) 222 (20,600), 328 (42,500); ν max 745 (m), 845 (m), 1060 (m), 1275 (m), 1570 (m), 1595 (m), 1655 (ms), 2230 (m) cm$^{-1}$.

Anal. Calcd. for $C_{19}H_{13}NO_3$: C, 75.24; H, 4.32; N, 4.62. Found: C, 75.16; H, 4.50; N, 4.57.

EXAMPLE 6

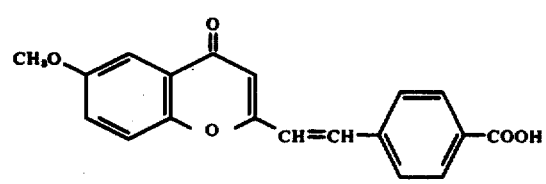

4-[2-(6-Methoxy-4-oxo-4H-1-benzopyran-2-yl) ethenyl]benzoic acid.

A mixture of 4g of 4-[2-(6-methoxy-4-oxo-4H-1-benzopyran-2-yl)ethenyl]benzonitrile and 100ml of 50% sulfuric acid was refluxed for 1 hr. with stirring. The mixture was chilled, and the precipitate washed with cold $H_2O$ and recrystallized from DMF, mp 293–97°; yield 1.5g (36%); λ max mμ (ε) 224 (18,800), 293 (17,200), 340 (42,200); ν max 770 (m), 975 (m), 1290 (ms), 1670 (ms), 1650 (ms), 1685 (s) cm$^{-1}$.

Anal. Calcd. for $C_{19}H_{14}O_5$: C, 70.80; H, 4.38. Found: C, 71.08; H, 4.34.

EXAMPLE 7

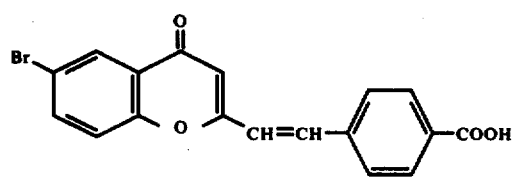

4-[2-(6-Bromo-4-oxo-4H-1-benzopyran-2-yl)erhenyl]-benzoic acid.

A mixture of 0.5g of 4-[2-(6-bromo-4-oxo-4H-1-benzopyran-2-yl)ethenyl]benzonitrile and 10ml of 50% $H_2SO_4$ was refluxed for 1 hr. The mixture was chilled, and the precipitate filtered, washed with cold $H_2O$, and recrystallized from DMF, mp 359° –62° ; yield 0.2g (18%); λ max mμ (ε) 270 (11,400), 334 (41,000); ν max 760 (m), 820 (m), 960 (m), 1280 (ms), 1610 (m), 1660 (s), 1690 (ms) cm$^{-1}$.

Anal. Calcd. for $C_{18}H_{11}BrO_4$: C, 58.24; H, 2.99. Found: C, 58.08; H, 3.05.

EXAMPLE 8

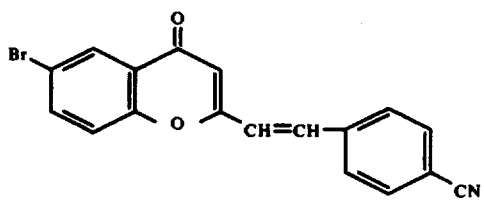

4-[(6-bromo-4-oxo-4H-1-benzopyran-2-yl)ethenyl]-benzonitrile.

A mixture of 3.9g of 5'-bromo-2'-hydroxy-2-(methylsulfinyl)acetohenone, 2.2g of p-cyanocinnamaldehyde, 50ml of toluene and 0.1ml of piperidine was refluxed for 4 hrs. The mixture was chilled, and the precipitate was filtered and recystallized from DMF, mp 275°-76°; yield 1g (20%); λ max mμ (ε) 223 (22,700), 273 (12,900), 330 (41,000); ν max 840 (m), 980 (m), 1280 (m), 1640 (m), 1660 (ms), 2240 (m) cm$^{-1}$.

Anal. Calcd. for $C_{18}H_{10}BrNO_2$: C, 61.39; H, 2.86; N, 3.98. Found: C, 61.18; H, 2.97; N, 3.99.

EXAMPLE 9

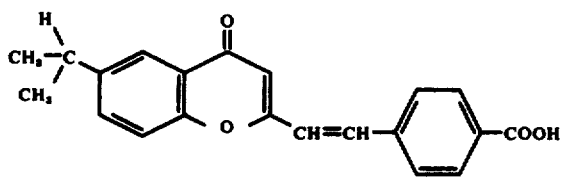

4-[2-(6-Isopropyl-4-oxo-4H-1-benzopyran-2-benzopyran-2yl)ethenyl]benzoic acid.

A mixture of 3g of 4-[2-(6-isopropyl-4-oxo-4H-1-benzopyran-2-yl)ethenyl]benzonitrile and 125ml of 50% $H_2SO_4$ was refluxed for 2 hrs. The mixture was chilled, and the precipitate filtered, washed with cold $H_2O$ and recrystallized from $CH_3CN$, mp 264°-65°; yield 2g (63%); λ max mμ (ε) 272 (11,900), 331 (43,600); ν max 765 (m), 1280 (ms), 1620 (s), 1640 (s), 1690 (s) cm$^{-1}$.

Anal. Calcd. for $c_{21}H_{18}O_4$: C, 75.43; H, 5.43. Found: C, 75.41; H, 5.45.

EXAMPLE 10

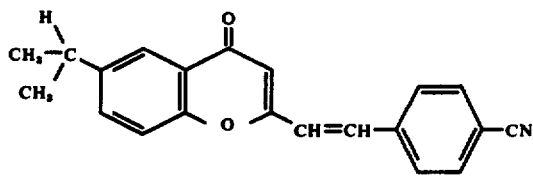

4-[2-(6-Isopropyl-4-oxo-4H-1-benzopyran-2-yl)ethenyl]benzonitrile

A mixture of 12g of 2'-hydroxy-Pb 5'-isopropyl-2-(methylsulfinyl)acetophenone, 7.8g of p-cyanocinnamaldehyde, 125ml of toluene, and 0.5ml of piperidine was combined and refluxed for 3 hrs. The solution was chilled, and the crystalline precipitate that was formed was filtered and recrystallized from $CH_3CN$, mp 189°-91°; yield 5g (31%); λ max mμ (ε) 220 (22,400), 276 (14,100), 328 (41,600); ν max 835 (m), 980 (m), 1580 (m), 1635 (ms), 2225 (m) cm$^{-1}$.

Anal. Cacd. for $C_{21}H_{17}NO_2$: C, 79.98; H, 5.43; N, 4.44. Found: C, 79.86; H, 5.42; N, 4.20.

We claim:
1. A compound of the formula:

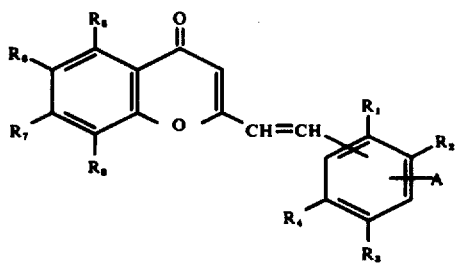

wherein $R_1$, $R_2$, $R_3$, $R_4$, $R_5$, $R_6$, $R_7$, $R_8$ are hydrogen, lower alkyl, halogen or lower alkoxy and A is COOH or CN.

2. A compound according to claim 1 which is 4-[2-(6-methoxy-4-oxo-4H-1-benzopyran-2-yl)ethenyl]benzonitrile.

3. A compound according to claim 1 which is 4-[2-(6-methyl-4-oxo-4H-1;1-benzopyran-2-yl)ethenyl]benzonitrile.

4. A compound according to calim 1 which is 4-[2-(6-methyl-4;1-oxo-4H-1-benzopyran-2-yl)ethenyl]benzoic acid.

5. A compound according to claim 1 which is 4-[2-(8-methoxy-4;1-oxo-4H-1-benzopyran-2;1-yl)ethenyl]benzoic acid.

6. A compound according to claim 1 which is 4-[2-(8-methoxy-4-oxo-4H-1-benzopyran-2;1-yl)ethenyl]benzonitrile.

7. A compound according to claim 1 which is 4-[2-(6-methoxy-4-oxo-4H-1-benzopyran-2-yl)ethenyl]benzoic acid.

8. A compound according to claim 1 which is 4-[2-86-bromo-4-oxo-4H-1-benzopyran-2-yl)ethenyl]benzoic acid.

9. A compound according to claim 1 which is 4-[(6-bromo-4-oxo-4H-1-benzopryan-2-yl)ethenyl]benzonitrile.

10. A compound according to claim 1 which is 4-[2-(6-isopropyl-4-oxo-4H-1-benzopyran-2-yl)ethenyl]-benzoic acid.

11. A compound according to claim 1 which is 4-[2-(6-isopropyl-4oxo-4H-1-benzopyran-2-yl)ethenyl]benzonitrile.

* * * * *